(12) United States Patent
Miqui

(10) Patent No.: US 9,999,483 B2
(45) Date of Patent: *Jun. 19, 2018

(54) ORTHODONTIC ARCH WIRE BRACKET WITH INTERCHANGEABLE LOCKS INCLUDING VARIABLE TOOTH POSITIONING CONTROL AND METHOD OF USING SAME

(71) Applicant: Carlos Eduardo Miqui, Sao Paulo (BR)

(72) Inventor: Carlos Eduardo Miqui, Sao Paulo (BR)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/446,469

(22) Filed: Jul. 30, 2014

(65) Prior Publication Data
US 2016/0030138 A1 Feb. 4, 2016

Related U.S. Application Data

(63) Continuation-in-part of application No. 11/382,846, filed on May 11, 2006, now Pat. No. 8,801,430.

(30) Foreign Application Priority Data

May 30, 2005 (BR) ..................................... 0502124

(51) Int. Cl.
*A61C 7/28* (2006.01)
(52) U.S. Cl.
CPC ................ *A61C 7/28* (2013.01); *A61C 7/287* (2013.01)

(58) Field of Classification Search
CPC .. A61C 7/28; A61C 7/287; A61C 7/30; A61C 7/34
USPC ........................................................ 433/8–17
See application file for complete search history.

(56) References Cited

U.S. PATENT DOCUMENTS

| 2,908,974 | A | * | 10/1959 | Stifter | A61C 7/12 433/16 |
| 4,180,912 | A | * | 1/1980 | Kesling | A61C 7/12 327/437 |
| 7,033,170 | B2 | * | 4/2006 | Cordato | A61C 7/287 433/10 |
| 8,801,430 | B2 | * | 8/2014 | Miqui | A61C 7/14 433/10 |

* cited by examiner

*Primary Examiner* — Edward Moran
(74) *Attorney, Agent, or Firm* — McKee, Voorhees & Sease P.C.

(57) ABSTRACT

An interchangeable lock is applied to a bracket, consisting of a lock designed for use in orthodontic treatment which is used in conjunction with an orthodontic bracket having a base bonded to the tooth in which the interchangeable lock should be frontally inserted. This same lock permits additional adjustments of the arch wire in regards to inclination, angulation or torque as there always be three walls forming a U-shaped slot, allowing the position of the arch wire to be controlled in relation to its inclination and angulation while maintaining the position of the bracket in relation to the tooth. It is possible to identify, modify and control the position of the tooth by contact adjustment with the arch wire at any time during treatment without the need to remove the arch wire or change or adjust the bracket.

1 Claim, 15 Drawing Sheets

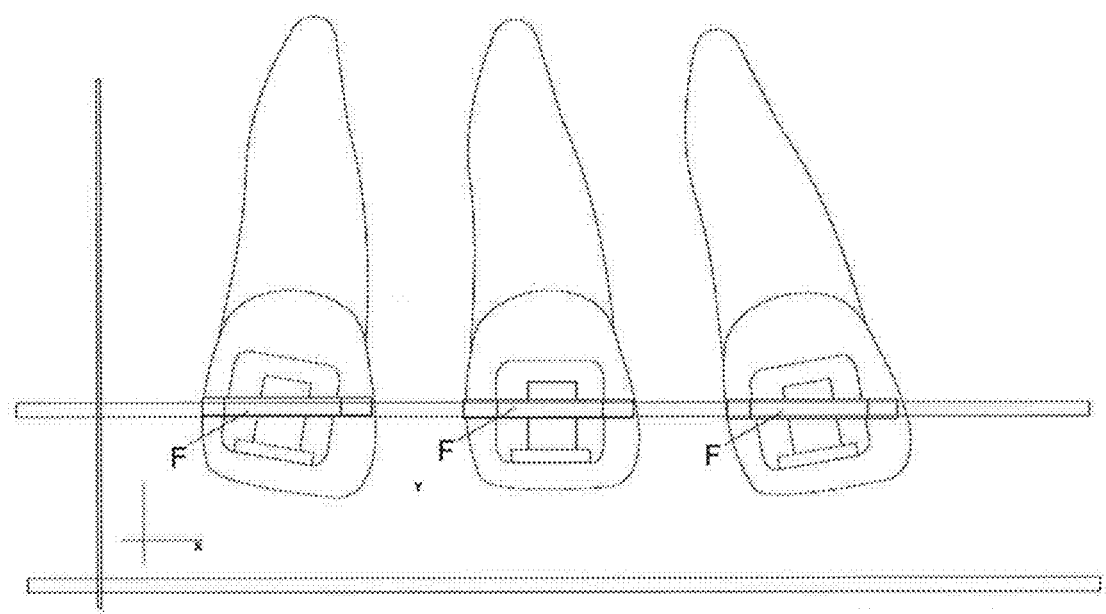
FIG. 12
FIG. 13A (PRIOR ART)
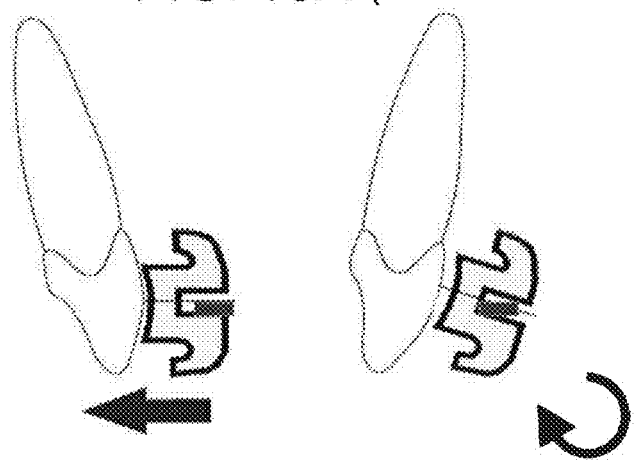

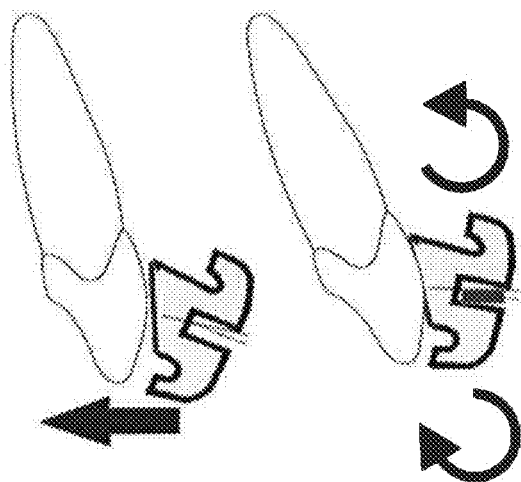
FIG.13B (PRIOR ART)
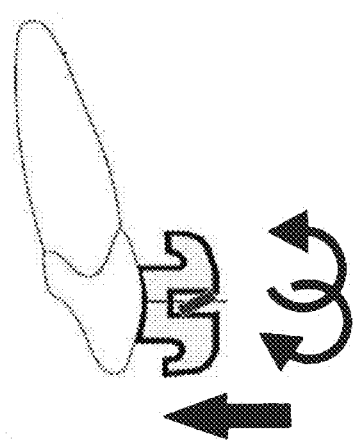

ORTHODONTIC ARCH WIRE BRACKET WITH INTERCHANGEABLE LOCKS INCLUDING VARIABLE TOOTH POSITIONING CONTROL AND METHOD OF USING SAME

CROSS-REFERENCE TO RELATED APPLICATION

This application is a continuation-in-part of U.S. patent application Ser. No. 11/382,846, filed May 11, 2006, which claims priority from Brazilian Application No. PI-0502124-3, filed May 30, 2005, the entire contents both of which are hereby incorporated by reference.

FIELD OF INVENTION

The invention herein relates generally to the field of orthodontic devices. More particularly the present invention relates to a bracket and lock system for retaining an orthodontic arch wire.

BACKGROUND OF THE INVENTION

It is known to those skilled in the art of orthodontics to use a bracket adhered to a tooth to engage an arch wire. The brackets, limited by current processes of manufacturing, have a constructive arrangement forming a body and a base (which may be composed of a single piece too) and, even with the development of new technology, little or almost nothing has changed, within the opening of the "channel" from the anterior face. The recent greatest revolution was the introduction of a lid or clip that holds the arch wire into the slot, actively or passively.

This traditional structure, although it is still being used extensively, is inconvenient because of the lack of flexibility when it comes to changing the tooth position established by the bracket, which means that if the orthodontist needs to change the torque or inclination of the bracket or arch wire, to adjust the position of the desired tooth, he or she will have to bend the wire or replace the bracket.

Another inconvenience (when it comes to the traditional twin brackets that are still being widely used in the market) results from the need for a metal or rubber ligatures to secure the wire to the bottom of the channel, due to the fact that the channel has an opening, with angulation and inclination predefined to each bracket, without possibility of change or modify except by changing the whole bracket. Finally, the only two ways to increase or reduce the force transmitted from the arch wire to the tooth is by changing the wire diameter or material composition.

There are also newer brackets known as self-ligature brackets, which have a lid that functions as the ligature. This system is divided between passive systems that do not push the arch wire against the bottom of the slot, and active or interactive systems, which push the arch wire against the bottom of the slot, some only from a certain arch wire diameter. However, this system follows the logic of having a single pre-defined angulation and inclination prior to bonding the bracket to the tooth, and cannot be modified except by the exchange of the bracket.

Stifter, U.S. Pat. No. 2,908,974 shows a bracket system of female and a male connecting member which are attachable in order to form an orthodontic assembly capable of receiving a certain arc wire, for example. In case there is a need to change the position of a tooth or bend this arc wire, it is always necessary to withdraw the male part, which is always taken laterally and then the removal of the arch wire; then the replacement of this arc, besides also requiring the use of a ligature (metallic or elastic) to hold the arch wire into the bracket.

The main focus of the invention proposed by Stifter: a male and female system that enables a change in position of the arch wire follows a traditional and extremely old way of thinking in the dental field, wherein a metal wire "ligature" attaches to a bracket with the aid of pliers and has its ends twisted, cut and accommodated. The current version of this ligature is made of elastic material. But this system, besides being laborious, accumulates dirt around the bracket, compromising hygiene and increasing the friction between the arch wire and the bracket, causing the need for greater use of force for tooth movement. Stifter also shows the possibility of changing the inclination of the male part that shows an opening to the buccal (or opposite to the female side) or a completely closed slot. However, this operation requires that the arch wire to the removed or all ligatures must be removed before and after the later placement of the arch wire in its position, re-tied one by one. In practice, one of the most common reasons for emergencies in the orthodontic practice is that these wire tips, that were initially cut, get out of the position where they were placed and hurt the inner lining of the mouth, causing injuries, pain and discomfort to the patient.

Cordato, U.S. Pat. No. 7,033,170 shows securing the arch wire by introducing a side "clip" in the slot of the bracket so as to combine the two fixed walls of the bracket together with the two movable walls of the "clip", forming a rectangular tunnel in which the arch wire is passed through, ruling out any possibility of adjusting the angulation of the tooth in relation to the vertical axis, in the internal and external sense. This also includes the use of a tighter or looser "clip", which together with the bracket, can give more or less freedom to the arch wire. This feature would allow the arch wire to be positioned with greater freedom in relation to the tooth, however without the characteristic of active control (i.e., determining whether the tooth will be moved left or right, forward or backward).

Another problem encountered is when the orthodontist faces crowded teeth that are the main aim of patient when asking for the orthodontist assistance, in order for the teeth to be correctly aligned in the oral cavity. Prior solutions would also have disadvantages in their techniques in most situations where there is a situation of dental crowding, since it is totally impractical for the technique of Stifter which brings the internal fitting member connecting male to the female bracket that can only be performed sideways due to the shapes of the parts and when the needed lock is required, one must use a ligature; the same occurs in Cordato, where the "clip" must be inserted on the inside via the laeral face of the part.

Therefore, the previous proposals have disadvantages in regards to their use that are overcome by the invention herein proposed. Significantly, its lock, besides having other advantages, is located externally and buccally or labially, without the need for additional ligature, allowing simultaneous control of the tooth position.

Regarding the torque control that refers to angulation of the tooth in respect to the vertical axis, in the lingual (internal) X buccal-labial (external) sense of the oral cavity and inclination control of the tooth in relation to its position in relation to the mesiodistal direction, we can conclude that Stifter could achieve this level of control, but the procedure requires removal of the arch wire, exchange of the male-part, arch wire replacement and relocation of the male part, which are extremely complex, laborious for the professional performing it and totally uncomfortable for the patient that will stay longer on the chair and will be much longer in the treatment room. In this scenario, the technique used by Cordato would never allow such angulation or inclination, since there are always 2 affixed walls of the bracket that join the 2 movable walls of the "clip", to then create the tunnel in which the arch wire will pass through, wherein this characteristic does not allow the total control to be achieved due to the absence of three-dimensional control.

BRIEF DESCRIPTION OF THE INVENTION

Analyzing the inconveniences mentioned above, the inventor, who is an active person in the orthodontic area, has created a versatile bracket and lock system which is able to meet the needs and unforeseen natural occurrences during an orthodontic treatment, i.e., a lock that can be suitable for varied possibilities.

An object of this invention comprises, generally speaking, in an interchangeable lock system, which is a new and fully differentiated part, with internal slots that besides the function of keeping the arch wire attached to the bracket, also has the characteristic of allowing a change on the tooth position to which the arch wire is related, through the bracket. This system has a lock that works superimposed to a orthodontic bracket allows the exchange for another chosen lock, varying the size, angulation or inclination of the "channel/slot" according to the relevant needs of treatment without changing the bracket or performing major adaptations or bending the wire (which has the responsibility to move teeth in the planned direction).

This exchange does not depend on the removal of the arch wire from its position or a change in position of the bracket. And, this exchange can occur at any time during treatment and how often the orthodontist deems it necessary as it does not require the replacement of the arch or the bracket, making the process extremely simple.

These locks can have their size or angulation or inclination of the "channel/slot" individualized in only one or in all of the three dimensions simultaneously.

Once the lock is superimposed on the bracket, one has a set of anatomical and more comfortable external lines. With referred lock, there is greater flexibility in regards to the use the same arch wire, it is possible to modify the amount of force transmitted by simply changing the interchangeable lock by one with a larger slot in order to increase the arch wire freedom and decrease the force applied or transmitted to the tooth or lock vice-versa; a lock with a smaller slot, with less arch wire freedom and increased force applied or transmitted to the tooth.

Thus, the present invention brings up a series of extraordinary advantages, of practical and functional natures, notably geared to achieving the optimization during treatment and greater patient comfort.

An interchangeable lock applied to a bracket, notably a lock developed for use in orthodontic treatments where an orthodontic bracket, which has its base bonded to the tooth, and this interchangeable lock which should be inserted in a frontal manner and can be engaged from upwards toward downwards and vice-versa, of the outside of the orthodontic bracket; which besides adding the functionality of connecting the arch wire to the bracket, this same lock still adds the property of allowing additional positive or negative angulation and inclination adjustments by replacing the lock for another locks with torque characteristics and/or different inclination from the original, allowing the tooth position to be controlled in respect to its angulation and inclination by the position expression to which it will be directed (the tooth) by means of contact between the arch wire and lock; and the arch wire, while by its construction characteristics, it also allows the arch wire to move through the slot practically without friction, wherein it is being possible to identify, modify and control the tooth position tooth by the contact adjustment with the arch wire.

The fact that the lock contains grooves (or as we will call from now and on, slots channel) inserted internally on its sidewalls, allows this to not apply pressure in the arch wire, reducing the friction between the lock, bracket and arch wire.

More specifically, for example, in the initial phase of treatment it is possible to have a bracket with a greater slot "channel" that, together with an arch wire of reduced diameter, gives the assembly greater flexibility and less power, which immediately increases patient comfort. Studies have also shown that lighter forces within biological limits can accelerate the rate of tooth movements. While in the final phase, exchanging the locks of the teeth will be performed where deemed necessary, by another lock with a reduced diameter, resulting in increased position control.

For a better illustration, in a practical example, a slot channel that is "0.040" high is associated with a wire with diameter of "0.014", composed of more elastic alloys, is extremely comfortable for the patient, whereas with higher freedom interface between the arch wire and slot associated with low friction, it allows faster and comfortable movements within biological limits. For such, one should also take into account the relative hardness of each material according to specific tables.

Still virtually illustrating the invention, after the first stage or initial stage, one would use an interchangeable lock which would have a intermediate height slot "channel" which, together with wires of greater diameter than the wires initially used, would allow greater control, ideal for this stage of treatment. For example, with a set of "0.022" as an intermediary lock force level or "0.016" height slot "channel" as a high lock force level with the same arch of "0.014" diameter: In this case, the freedom between the wire and the slot walls is minimal and control is maximized, and the transmission of power becomes to the tooth becomes more efficient. However, this system still uses very mild forces compared to the use of arch wires of larger caliber.

Or, when a slightly larger force is desired, or to increase the level of control at the final stages, one could opt for arch wires of intermediate strength as of "0.014"ב0.025" or "0.016"ב0.025" associated with this same lock with slot channel with a height of "0.016".

The illustration of FIG. 1 represents the freedom of positioning of an arch wire of "0.014" or "0.014"ב0.025" in a lock with slot of "0.040" or "0.22" or "0.16" height. Thus, in a "0.040" slot, freedom is extreme. With greater freedom, a smaller force is transmitted to the tooth and this set becomes more comfortable. Whereas, when used with a lock with a slot height of "0.016", freedom is minimal; control is increased, however, with the use of elastic arches, it is possible to combine biological forces with the maximum control of tooth.

Finally, one can individualize each tooth on a specific and customized manner, according to the patient needs, i.e., in case of the need of a distinct torque for a specific tooth, one can simply use the same wire (without the folds or bends) and change the locks on teeth wherein it is desired to proceed with further individualization. More particularly, it is possible to have variations in the final stages of the treatment in which the tooth can start with a higher torque lock, for example 22°, for mechanical retractions where the additional torque would serve to compensate any loss of torque of the tooth to be moved by its own mechanics and finalize with a lower torque lock, e.g. 15° or 7° which would be closer to the ideal tooth positioning, without changing the bracket altogether, which could cause damage to tooth enamel, and a simply change the interchangeable lock (with a torque 22° to another 15° or 7° without the need for removing or making the bends in the arch wire, when the orthodontist deems necessary to proceed quickly and accurately). This concept is explained in Figures.

Another possibility, as shown in FIG. 1A is to move forward to the final stage by combining a "channel" of smaller size with a smaller diameter arch wire with little or no play, but more rigid, without the need to effectively increase the strength level and consequent patient discomfort, as for example, a channel of "0.016" tall with an stainless steel arch wire of "0.016"דּ"0.025". That is, instead of using an arch wire of stainless steel with a larger diameter, for example, a "0.021"דּ"0.025" slot in a bracket with "0.022" high, with relative hardness degree of 2176 according to a specific table, an titanium molybdenum arch wire of "0.016"דּ"0.022" can be used with relative hardness degree of 1130, nearly half of the force, but with equivalent control. Recalling that the smaller the force applied, the greater comfort for the patient.

Theoretically, one could even go through all of the stages of the treatment with practically using the same memory arch wire, which are extremely comfortable for a low applied force, reaching the final stage, simply by changing the locks. Even during the intermediary mechanicals, one can obtain great current mechanical variables, without the undesirable side effects.

The present invention provides the advantages of speed, versatility, customization, accuracy and optimization.

DESCRIPTION OF THE DRAWINGS

The invention will be explained with reference to the accompanying drawings, in which are represented:

FIG. 12 is a front view of the same interchangeable lock shown in FIG. 11 applied to the bracket, representing the 3 different locks for the same tooth, but with distinct functions.

FIG. 13A is a graphic showing side views of a tooth illustrating a basic prior art application showing the sequence of the movement of retraction of anterior teeth, wherein loss of torque control occurs during retraction.

FIG. 13B is a graphic showing prior art options for dealing with the loss of torque control, including changing the bracket or adding a wire bend.

DETAILED DESCRIPTION OF THE INVENTION

Figure 16:
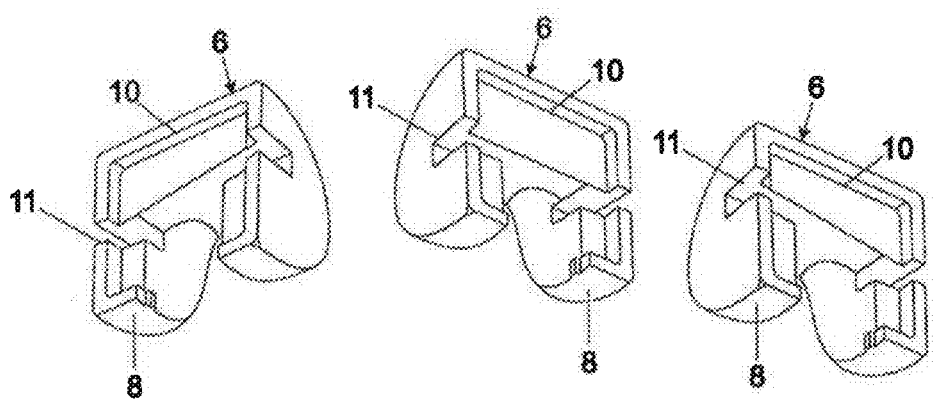
FIG. 16 is a schematic exploded side view showing alternative inclinations of the locks from the back side.

A plurality of locks (6) with different slot channel angulations, inclinations and dimensions (11) located on its side walls (8) is shown in FIG. 16. Once superimposed on a corresponding bracket (2), it creates optimal paths for the passage of wires (F) of different diameters by simply swapping the locks (6) to adjust the channels (11) according and based on the treatment necessities, remaining the same bracket bonded to the tooth during the whole treatment.

The bracket (2) has as features an anatomical base (4) which allows its bonding to the tooth or can be bonded directly or welded to an additional base to facilitate its affixation to the tooth (not shown in the drawing). This base (4) contains angulation and inclination related to the tooth to be bonded while containing an opening or slot (V) for the insertion and passage of an arch wire. This bracket (2) also has the ability to receive different types of locks (6) with channels (11) of different angulations, inclinations, heights and depths, chosen according to the preference of dentist in using mechanicals or techniques as a matter of choice. While it can receive different locks (6), said bracket (2) can be kept in its initial position from the beginning to the end of treatment procedure.

Therefore, the present invention is noted for the extreme flexibility achieved in orthodontic treatments, in which it is possible to be applied a variety of interchangeable locks (6) to said bracket (2) and also to direct the control of angulations and inclinations of the teeth individually and for the desired amount of time, during the course of treatment.

Among the various possible combinations between the bracket and locks (6), it should be emphasized the fact that the bracket and interchangeable lock (6) are perfectly adjustable, so that once overlapped, the upper portion (9) of the bracket conforms through the recess (10) on the inner portion of the lock (6). Moreover, after a proper fit, the lock (6) is naturally aligned to the axis (E) of the bracket so that the "channel" (11) provided in the walls (8) of said lock (6) in the desired embodiment of the invention, altogether with the opening (V) of the central bracket, formed by the orthogonal projection (5), allowing the passage of traction wires (F), and after the superimposition of the lock, it takes an external rounded ergonomic shape more comfortable to the patient.

In this foregoing principle, from the same bracket it is possible to use various combinations of locks (6) each one with different slot channels (11) located in lateral recesses (11) of variable size, inclination and angulation. For example, to obtain a neutral torque, a lock with channels (11) is used within the dimension chosen and compatible with the arch wire or traction element. This neutral torque is obtained with the expression of torque by the action of the arch wire in contact with the channels (11) and bracket. Neutral torque is denominated when the channel/slot (11) is parallel to the horizontal occlusal plane when the full expression of torque by the action of the arch wire in contact with the lock and the bracket, and the tooth is in traditional position and accepted by the class as finalized. To obtain angulation or additional positive torque while keeping the same bracket (2), the lock will contain channels (11) on the side (8) of the lock with angulation toward counter clock wise to the vertical middle axis of the face, when compared to its neutral position. And to obtain angulation or negative torque, said channels (11) has a angulation toward clock wise to the vertical middle axis of the face, when compared to its neutral position.

The lock (6) once coupled to the bracket (2) besides allowing to direction the torque, also allows changing the inclination. Starting from a neutral inclination, a variation of inclination can be added either positively or negatively in accordance with the desired and chosen among a variety of locks. It is considered a neutral inclination when the slot is in a perpendicular position to the long axis of the face after the expression of the total inclination determined by the action of the wire in contact with the slot and bracket; and the tooth is in traditional position and accepted by the class as finalized. By simply exchanging the lock (6) that, in the neutral position and the slot which is perpendicular to the long axis of the face; when choosing an additional right inclination, this extra inclination slot will have an inclined position to the right with respect to the slot with neutral inclined position. And the inverse, from the moment that the orthodontist chooses an additional left inclination, this slot with an extra left inclination to the position related to the slot with neutral inclination to the left.

Another possibility which relates to the possibility of flexibility in the dimension of width, depth and height; it means, it is possible to have a lock (6) adapted to all possible dimensions, depending on the choice of the amount of control or positioning of the tooth as well. The choice of this dimension depends only on the mechanics chosen by the dentist to treat his patient.

If it is chosen to have an additional freedom by utilizing an arch wire of determined given size and material, the dentist only has to use a lock with increased slot size. In this manner, the arch wire applies a lighter force to the tooth, with greater patient comfort and has less control of its positioning for a greater freedom of motion of the arch wire inside the slot of the lock. If it is chosen to have minor additional freedom to use arch wire of specific caliber and material, the dentist only has to use a lock with reduced slot size. In this manner, the arch wire apply heavier force to the tooth with less patient comfort and have greater control of their position by less freedom of motion of the arch wire inside the slot of the lock.

The lock (6), when superimposed on the bracket (2) without the traction wire (F) obviously does not alter the relative position of the teeth, considering it does not suffer any kind of force. Therefore, with the locks (6) and different torques, it is possible that, with the same bracket (2) and varying only the locks (6), to take the tooth to a positive extreme position, passing through the neutral position to an extreme negative.

With the same principle, one can get an extreme flexibility in the inclination variation, passing from an extreme right, neutral and to the extreme left simply and quickly by changing the locks (6) in the desired teeth.

Another possibility is the movement of retraction or other type of motion wherein a force is applied in order to causes what we call a side effect of loss of control of the positioning, normal in cases of extraction, so that the lock (6) allows to change the torque only when necessary, i.e., instead of replacing for a bracket with higher torque to compensate for the loss of inclination/torque motion and, change it during finalization, one can use the lock (6) with a higher torque only during the retraction phase and then return to normal torque by simply changing the lock (6).

Another possibility applied to the lock (6) is the possibility of small changes in the position of the teeth in the finalization or mechanics of the treatment. Even subtle changes, when performed inside the mouth, can be extremely laborious in regards for the need to properly bend the traction wire traction and extremely uncomfortable for the patient.

Figure 1A:
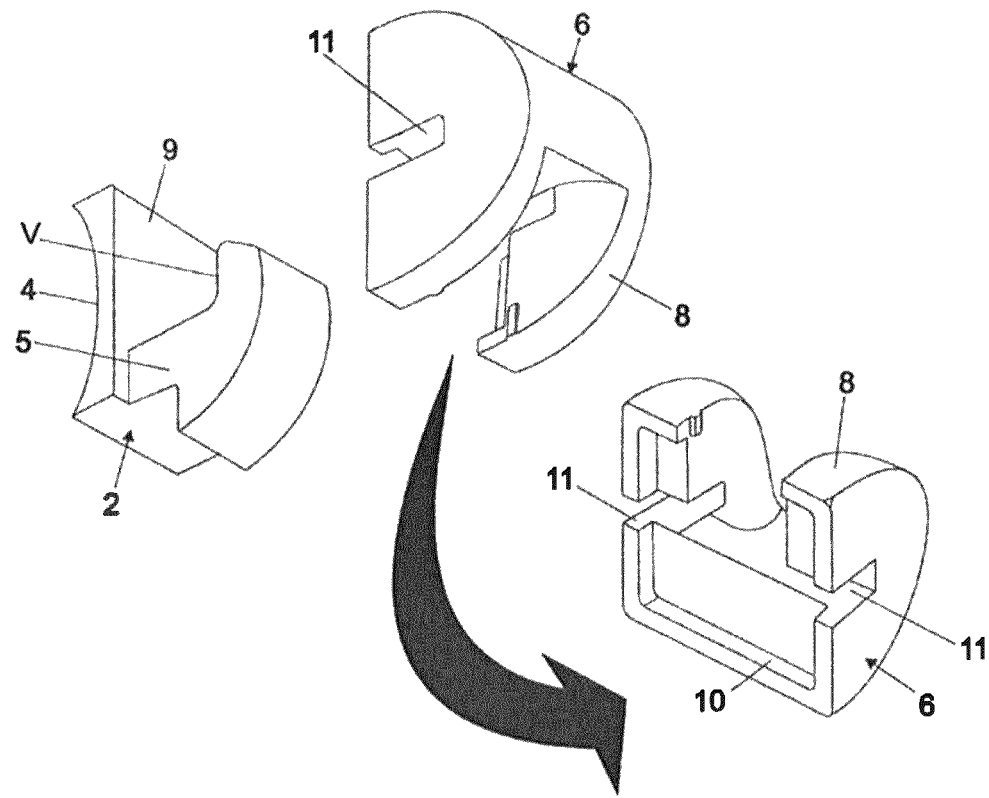
FIG. 1A is a perspective view of a base and interchangeable lock, showing the interchangeable lock generally from the front and from the rear.
Figure 1B:
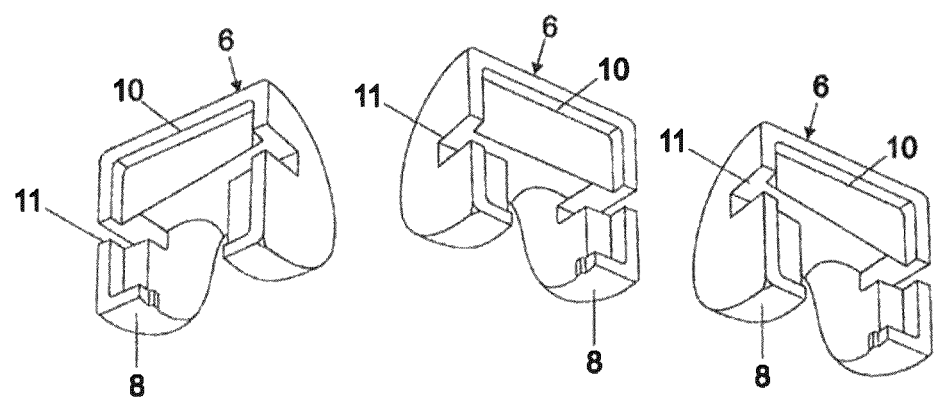
FIG. 1B is a perspective view of a of the back of the interchangeable lock, showing the interchangeable with different inclinations.
Figure 2A:
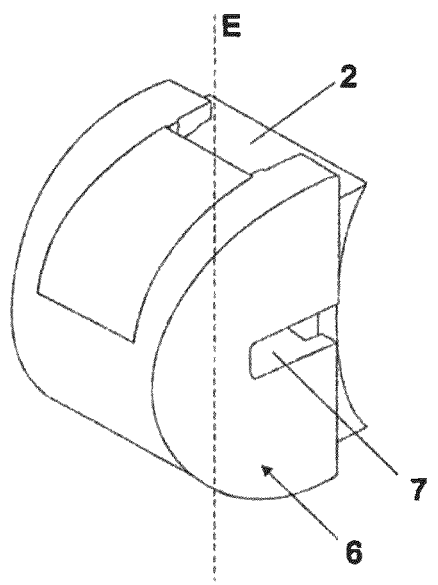
FIG. 2A is a perspective view of the base and interchangeable lock of FIG. 1 with the lock installed on the base.
Figure 2B:
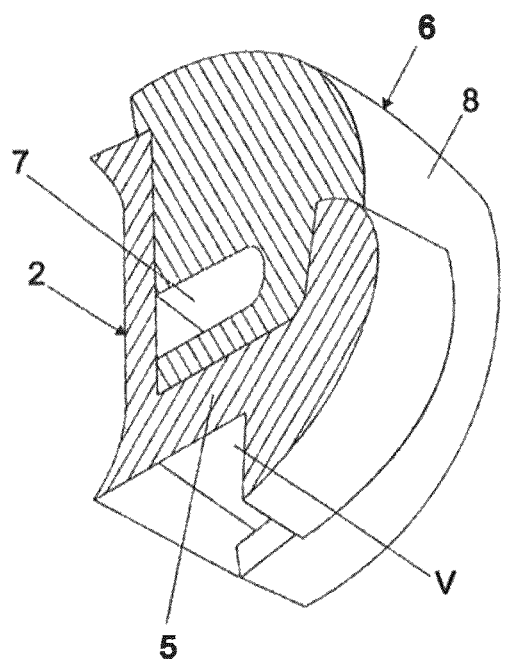
FIG. 2B is a cross-sectional view of the base and interchangeable lock of FIG. 2A taken along line E.
Figure 3:
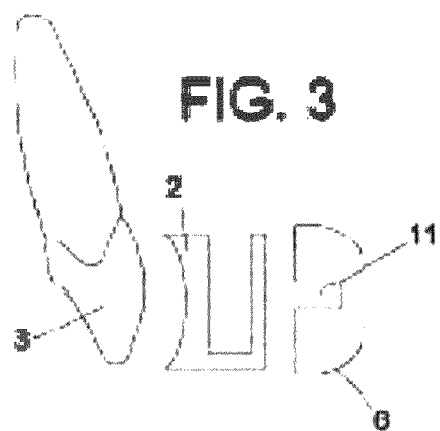
FIG. 3 is a side exploded view of a tooth, base and lock; wherein the lock has a neutral torque angulation configuration.
Figure 4:
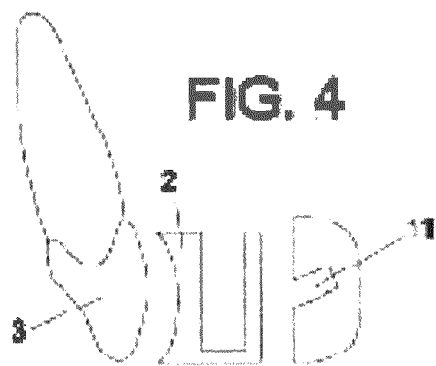
FIG. 4 is a side exploded view of a tooth, base and lock; wherein the lock has a negative torque angulation configuration.
Figure 5:
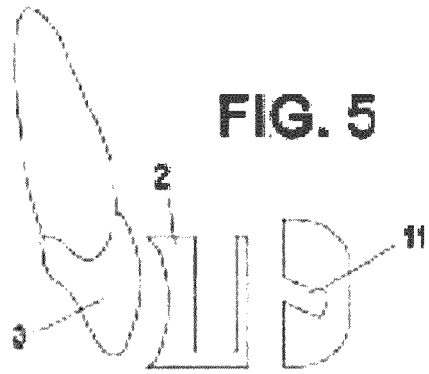
FIG. 5 is a side exploded view of a tooth, base and lock; wherein the lock has a positive torque angulation configuration.
Figure 6:
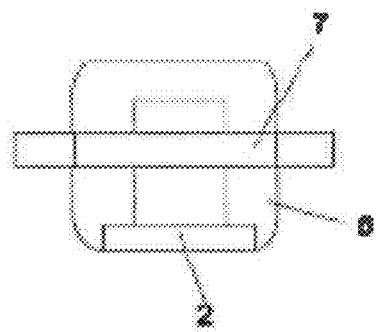
FIG. 6 is an internal view of a base and interchangeable lock wherein the lock has slots configured to deliver a neutral inclination of the tooth.
Figure 7:
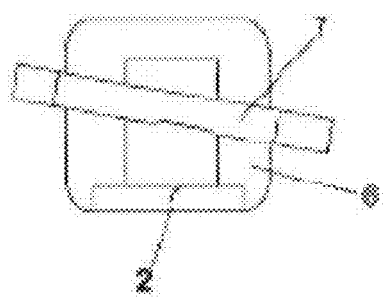
FIG. 7 is an internal view of a base and interchangeable lock wherein the lock has a configuration that will deliver a left side inclination of the tooth.
Figure 8:
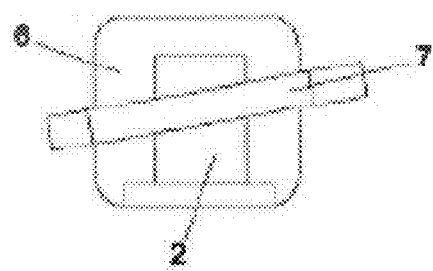
FIG. 8 is an internal view of a base and interchangeable lock wherein the lock has a configuration that will deliver a right side inclination of the tooth.
Figure 9:
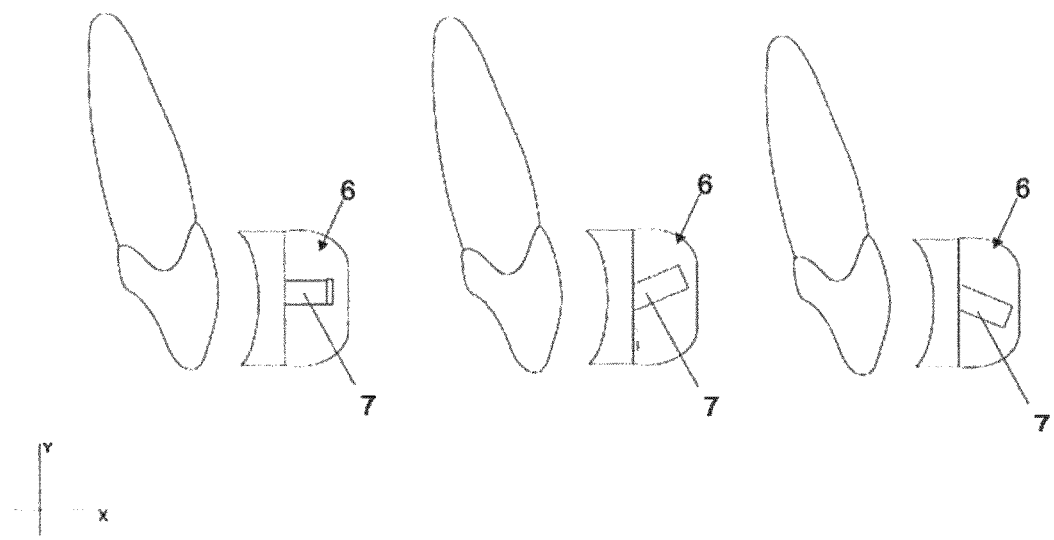
FIG. 9 shows a basic application where the schematic side view shows the tooth, the bracket and lock to obtain the neutral, additional negative and additional positive.
Figure 10:
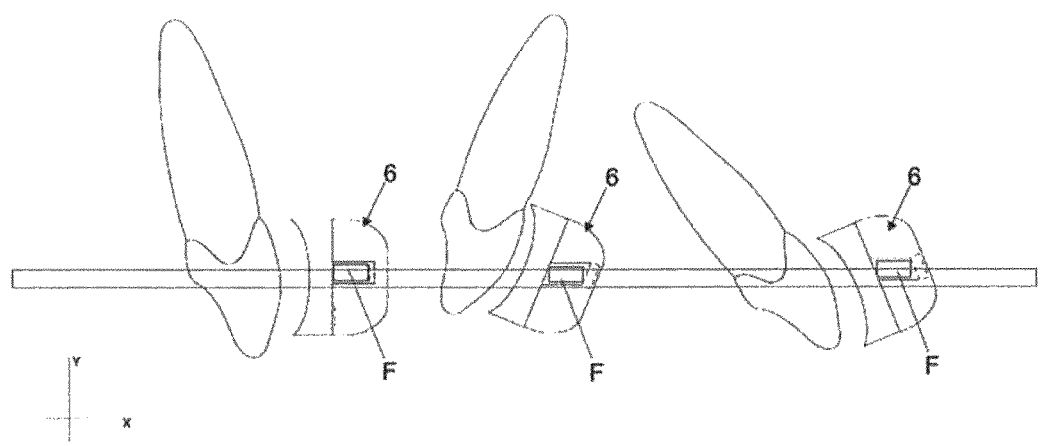
FIG. 10 is a side view of the same interchangeable lock shown in FIG. 9 applied to the bracket, representing the 3 different locks for the same tooth, but with distinct torques angulations expressed.
Figure 11:
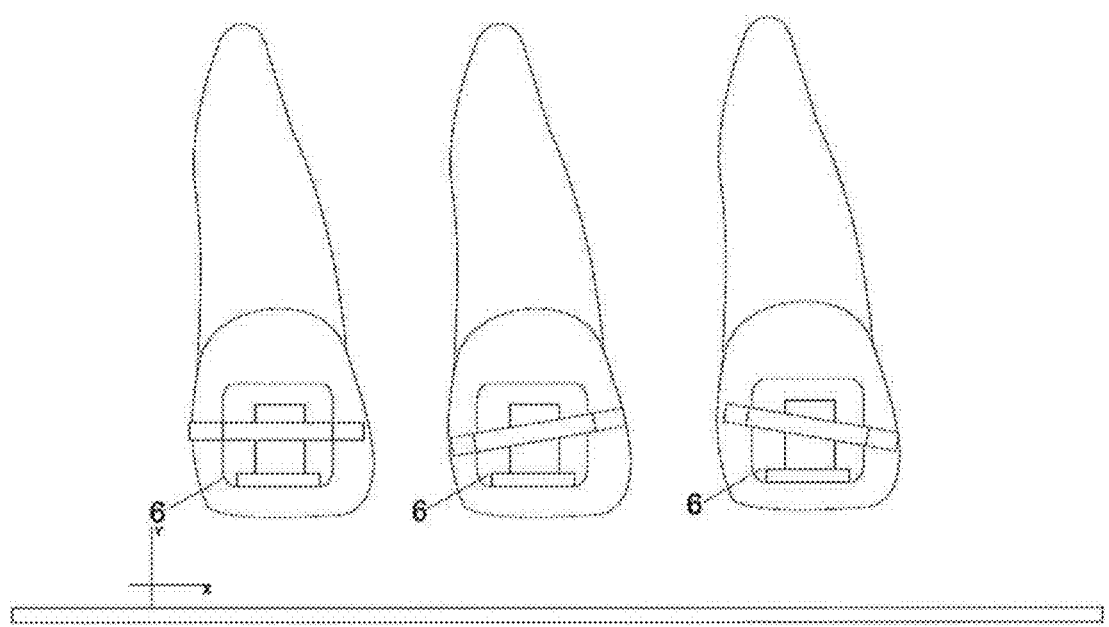
FIG. 11 is a schematic front view showing the base and lock to obtain a neutral inclination, additional right and additional left additional.

FIG. 9 illustrates a basic application where the schematic side view shows the tooth, the bracket and lock to obtain the neutral, additional negative and additional positive. In the first picture on the left it is shown the tooth, the bracket and a lock with neutral torque in its final position relative to the tooth in neutral/no bends wire position. In second position in the middle, it is shown the tooth, the bracket and a lock with torque or additional negative angulation showing their relative position to the tooth, prior to its application and its position relative to the occlusal plane. The additional negative torque will be applied to the tooth by inserting the lock to the bracket and the expression of the torque by the return of the arch wire to its neutral position, without bends and parallel to the occlusal plane. In the third position on the right it is shown the tooth, the bracket and a lock with torque or additional positive angulation showing their relative position to the tooth, prior to its implementation and its position relative to the occlusal plane. The additional positive torque will be applied to the tooth by inserting the lock to the bracket and the expression of the torque by the return of the arch wire to its neutral position, without folding and parallel to the occlusal plane;

FIG. 10 is a side view of the same interchangeable lock showed on FIG. 9 applied to the bracket, representing the 3 different locks for the same tooth, but with distinct torques angulations expressed. In the first position on the right showing a torque of additional positive angulation showing its final position on the arch wire in a neutral/no bends position. In the left, showing a neutral torque or standard angulation in its final position relative to the arch wire in neutral/no bends position. In the middle, it is shown a torque of additional negative angulation showing its final position on the arch in a neutral/no bends position. In this representation we show the teeth in 3 different positions with the lock having expressed its final position by the action of the arch wire, and having as the common point the straight wire through the slot channels of the brackets on each tooth;

FIG. 11 shows a basic application where a schematic front view shows the base and lock to obtain a neutral inclination, additional right and additional left additional. In the first picture on the left, it is shown the bracket and a lock applied in a neutral inclination in its final position in relation to the tooth in a neutral/no bend wire position. In the second position, it is shown the bracket and a lock applied with additional left crown inclination showing their relative position to the tooth and their position in relation to the occlusal plane prior to the inclination expression. The additional inclination to the right will be applied to the tooth by inserting the lock to the bracket associated to the use of an elastic arch and the expression of addiccional inclination by the return to its neutral position or no bends and parallel to the occlusal plane. In third position to the right, it is shown the bracket and lock applied with additional right crown inclination showing its relative position to the tooth and its position in relation to the occlusal plane. The additional inclination to the right will be applied to the tooth by inserting the lock to the bracket associated to the use of an elastic arch and the expression of inclination by the return of the arch wire to its neutral position or no no bends and parallel to the occlusal plane.

FIG. 12 is a front view of the same interchangeable lock shown in FIG. 11 applied to the bracket, representing the 3 different locks for the same tooth, but with distinct functions. The first position on the left showing an additional crown inclination to the left showing its final position on the arch wire in neutral position/no bends wire. The second on the middle showing a neutral position or perpendicular inclination showing its final position on the arch in neutral/no bends wire position. The third position on the right, showing an additional crown inclination to the right showing its final position on the arch in neutral/no folding position. In this representation, It is shown the teeth in 3 different positions with the lock having expressed its end position by the action of the arch wire, and having as the common point the straight wire through the slot channels of the brackets on each tooth;

FIG. 13A illustrates a basic application showing the sequence of the movement of retraction of anterior teeth associated with use of the new lock in relation to a dental arch (for example in a case with premolar extraction or correction of Class II).

The mechanical principle is: to apply force in order to bring the anterior set of teeth, because these teeth have its center of resistance located above the point of force application; they will have a tendency to loss torque control, which would result in lingual inclination of this tooth.

FIG. 13B shows prior art options for dealing with the loss of torque control, To avoid this side effect of movement, one could work in two manners: the first option would be to apply a distalization force and simultaneously apply a compensation bend to arch wire to counterbalance this unwanted movement. To place this bend in a controlled manner, would require the dentist to remove the arch wire from its position, he would have to have the ability and control to apply the band, and replace this arch wire to its position. This process is very time consuming and additional skill is required. At the end of the process, with the tooth retracted and in an adequate end position, the dentist would have to re-adjust or replace the arch wire again to prevent this additional torque applied to the arch wire to be expressed to the tooth, now in a proper finishing position. Another option, as shown on the left as option 1, would be exchanging this bracket during the retraction process and exchange it again for the finishing stage. This process requires a lot of additional time, spent due to the use of additional brackets, and offers risk to the enamel of the patient's tooth, by extracting it and re-bonding it to achieve this goal.

Figure 13C:
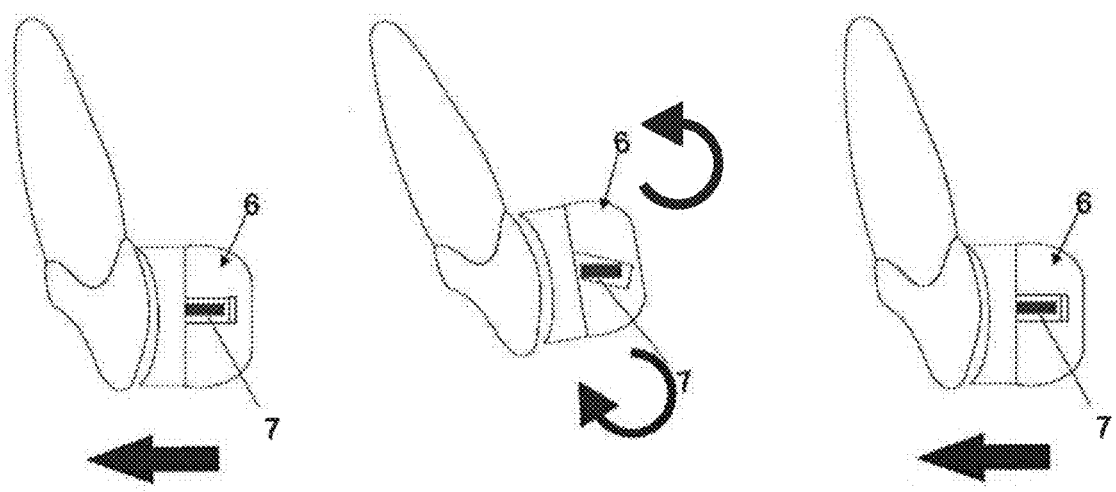
FIG. 13C is a graphic showing use of the present invention wherein the torque can be adjusted by changing the lock, without removing or bending the wire.
Figure 14:
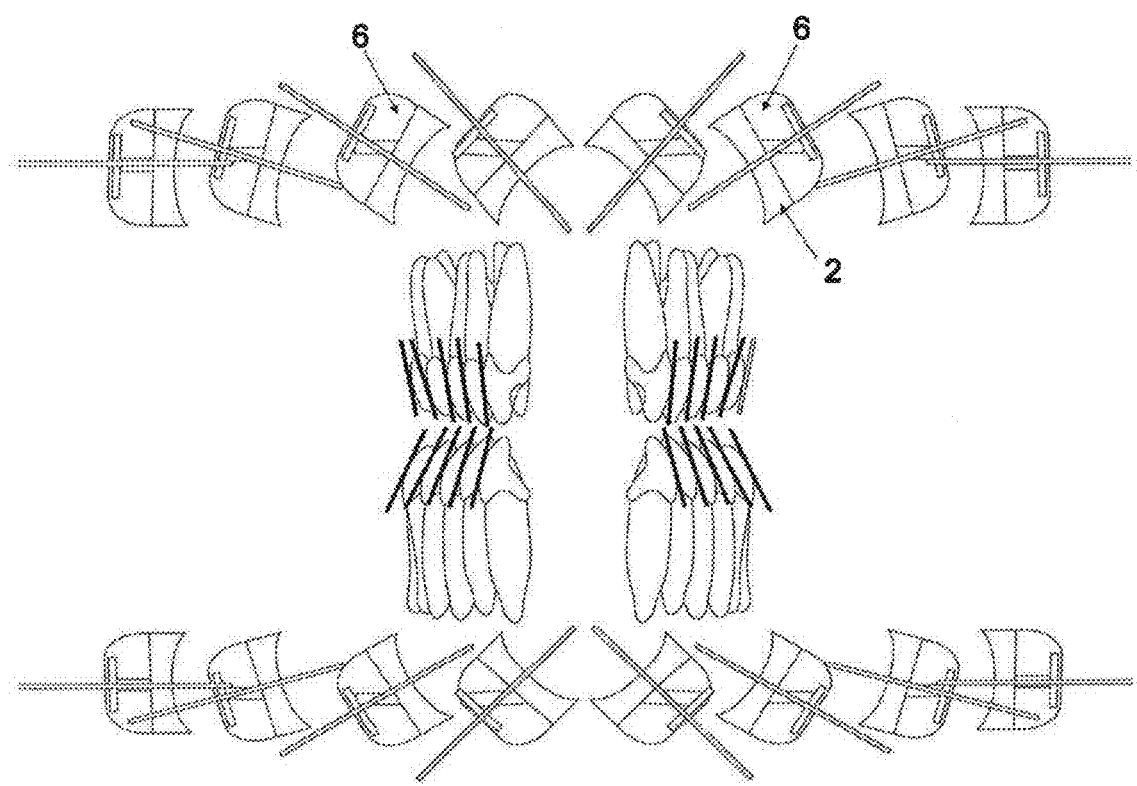
FIG. 14 is a schematic showing a basic application showing small changes in teeth positioning as in the finishing mechanics of treatment.

FIG. 13C illustrates the object of this invention, the interchangeable lock, we could simply replace the lock for one with additional torque to avoid loss of torque control angulation only during the distalization phase, returning the lock with adequate torque at the end of the movement. This process is extremely fast and does not require replacement or bending the arch wire or exchanging and resealing the bracket because the bracket would still be attached to the tooth from beginning to end of the treatment;

FIG. 14 illustrates a basic application showing small changes in teeth positioning as in the finishing mechanics of treatment. All of these inclination or torque variations are possible in all teeth by simply changing the lock without the need of exchanging brackets or bends in the arch wire.

Figure 15:
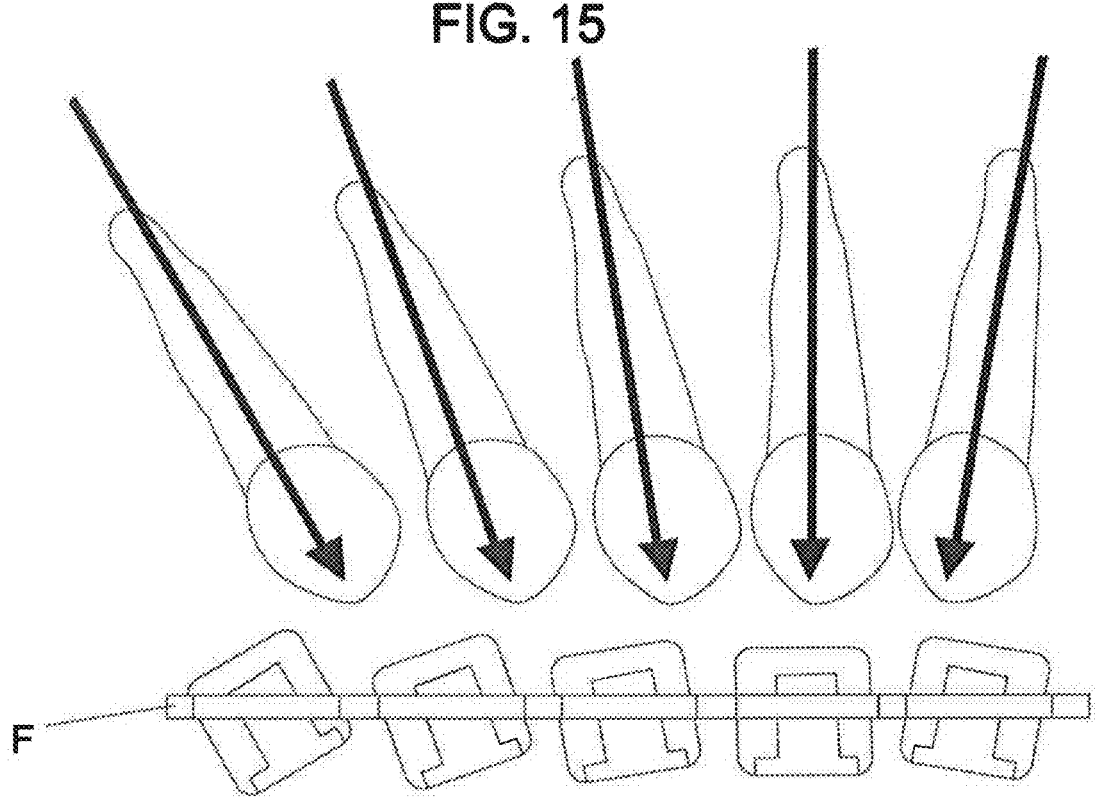
FIG. 15 is a schematic illustrating the possibility of flexibility in relation to the lock inclination of the tooth relative to its position in the dental arch.

FIG. 15 illustrates a basic application showing the possibility of flexibility in relation to the lock inclination of the tooth relative to its position in the dental arch. All this variation of the inclinations are possible in all teeth by simply changing the lock without the need of exchanging brackets or bends in the arch wire.

FIG. 16 illustrates the lock in a schematic exploded side view showing alternative inclinations of the locks from the back side.

Figure 17:
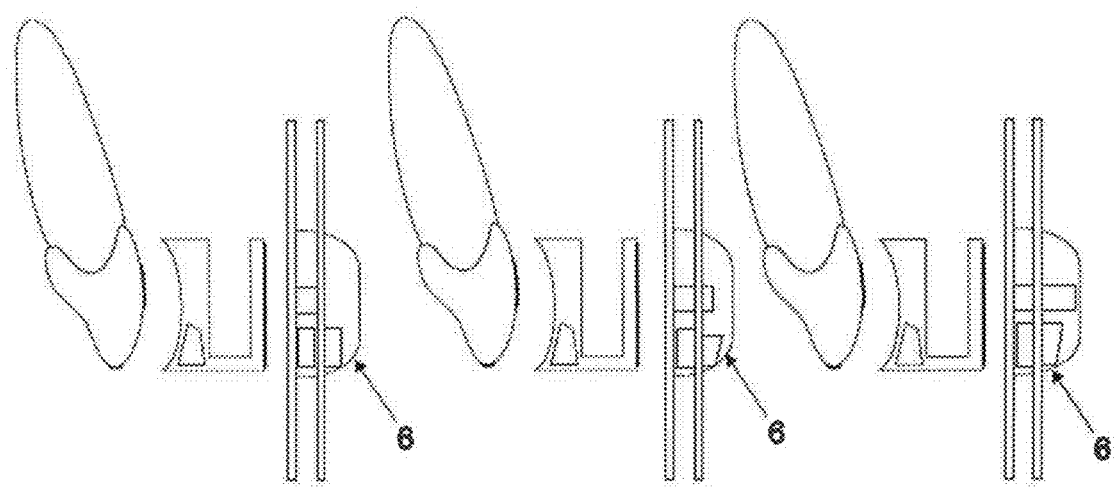
FIG. 17 shows the lock in a schematic exploded side view showing alternative width of the locks.

FIG. 17 shows the lock in a schematic exploded side view showing alternative width of the locks. This feature allows the degree of freedom of the anterior and posterior to be chosen for the arch wire in relation to the tooth. If it is desired a closer arch wire to the tooth or with less freedom, it is used a lock with smaller width, whereas if greater freedom is aimed, a lock with increased width is chosen.

Figure 18:
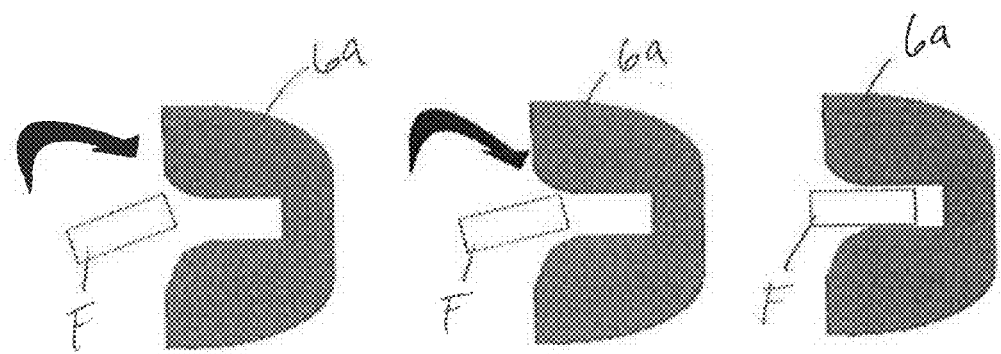
FIG. 18 shows an embodiment of the lock that includes a tapered opening to guide the arch wire into the slot of the lock.
Figure 19:
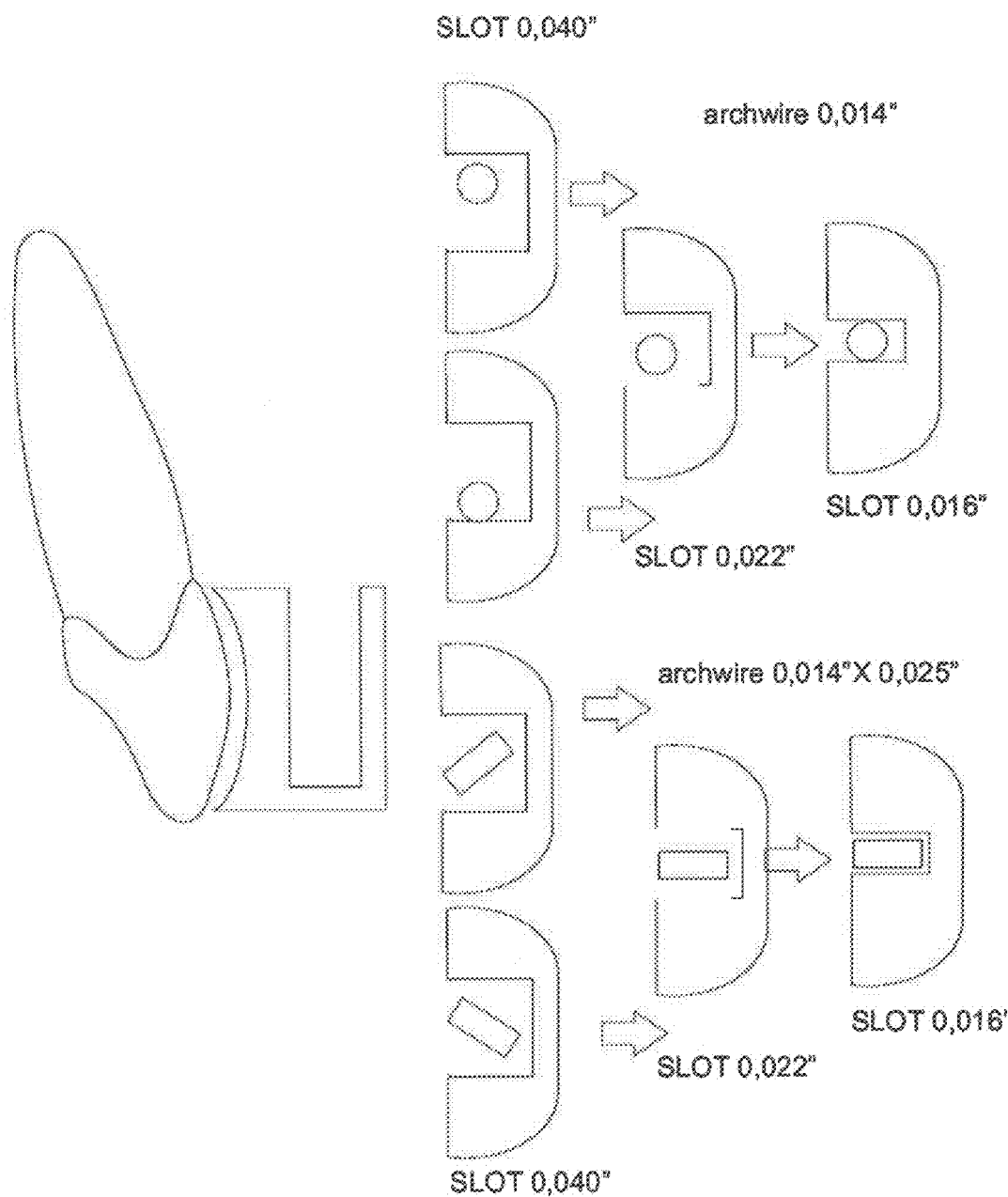
FIG. 19 shows a base for attachment to a tooth and a plurality of interchangeable locks.

FIG. 18 shows an embodiment of the lock (6*a*) that includes a tapered opening (O) to guide the arch wire F into the slot 11 of the lock (6*a*). The entrance or opening of the lock has a tapered shape, with the opening out, aiming to guide the arch F to the bottom of the slot, i.e., when the arch is tilted or angled with respect to the slot, the entry of this arc will be facilitated by the tapered shape of the slot of the lock. The walls of the tapered portion will guide the arch wire from the entrance to the end of the slot where the angulation and inclination are set.

These are just some of applications that are facilitated by the use of interchangeable locks system.

What is claimed is:

1. An orthodontic bracket system comprising:
 a plurality of interchangeable locks (6);
 a base (2) adapted to receive each of the plurality of interchangeable locks (6), the base having a rear surface (4) adapted to be adhered to a tooth, the base having a front surface opposite from the rear surface, an orthogonal projection (5) extending from the front surface of the base, the orthogonal projection having a forward extending portion extending from the front surface and a vertical portion extending generally vertically from the forward extending portion spaced apart from the front surface of the base, whereby the front surface of the base, the forward extending portion of the orthogonal projection and the vertical portion of the orthogonal projection form a gap (V);

each of the interchangeable locks (6) including a body and a first vertically oriented wall (8) extending from the body and a second vertically oriented wall (8) spaced apart from the first vertically oriented wall, wherein a first transverse slot (11) is formed in the first vertically oriented wall and a second transverse slot (11) is formed in the second vertically oriented wall, wherein said first and second slots are open towards a rear of the lock, wherein said first and second slots have an incline angle, wherein said first slot has a first depth, wherein said second slot has a second depth, and wherein the first slot has a first relative height and the second slot has a second relative height, and wherein the incline angle, slot depths, and relative slot heights vary between each of the plurality of interchangeable locks; and wherein each of the interchangeable locks attaches to the base with the orthogonal projection (5) of the base (2) received in the space between the first and second vertically oriented walls (8) of the lock (6), and the rear of the lock in close engagement with the front surface of the base wherein the first and second slots and the gap form a traction wire retaining groove; and wherein a direction of torque applied to the tooth is determined by the incline angle, the depths of the slots, and a difference between the relative heights of the slots which vary between each of the plurality of interchangeable locks; and wherein the orthogonal projection has a rounded exterior surface and each of the plurality of locks has a complementary rounded external shape that matches and aligns flush with the rounded exterior surface of the orthogonal projection to form a smooth outer surface of the base and lock.

\* \* \* \* \*